United States Patent [19]

Kubo et al.

[11] 4,309,341
[45] Jan. 5, 1982

[54] METHOD FOR PURIFYING α-L-ASPARTYL-L-PHENYLALANINE LOWER ALKYL ESTER

[75] Inventors: Masashige Kubo; Yuji Nonaka, both of Shin-nanyo; Keiichi Kihara, Tokuyama, all of Japan

[73] Assignees: Sagami Chemical Research Center; Ajinomoto Co., Inc., both of Tokyo; Toyo Soda Mfg. Co. Ltd., Shin-nanyo, all of Japan

[21] Appl. No.: 138,728

[22] Filed: Apr. 9, 1980

[30] Foreign Application Priority Data

Apr. 10, 1979 [JP] Japan ................... 54-43274

[51] Int. Cl.$^3$ ........................................... C07C 103/52
[52] U.S. Cl. ............................................. 260/112.5 R
[58] Field of Search ................................ 260/112.5 R

[56] References Cited
U.S. PATENT DOCUMENTS 3,798,206 3/1974 Uchiyama et al. ............ 260/112.5 R
3,798,207 3/1974 Ariyoshi et al. ............. 260/112.5 R
3,962,207 6/1976 Uchiyama et al. ............ 260/112.5 R

OTHER PUBLICATIONS

A. Yasutaki, et al., Bull. Chem. Soc. Japan 50, (1977) 2413-2416.
J. W. Bridges, et al. Progress in Drug Metabolism vol. 2, 219-222 1977.

*Primary Examiner*—Delbert R. Phillips
*Attorney, Agent, or Firm*—Armstrong, Nikaido, Marmelstein & Kubovcik

[57] ABSTRACT

A method for purifying an α-L-aspartyl-L-phenylalanine lower alkyl ester containing impurities. The α-L-aspartyl-L-phenylalanine lower alkyl ester is brought into contact with a Cl-type anion exchange resin in an aqueous medium to have the impurities adsorbed by the anion exchange resin. The impurities contained in the α-L-aspartyl-L-phenylalanine lower ester, particularly diketopiperazine and α-L-aspartyl-L-phenylalanine are selectively and easily removed. The desired matter thus can be easily recovered and disposal of waste liquid, etc. can also be carried out without difficulty.

4 Claims, No Drawings

METHOD FOR PURIFYING α-L-ASPARTYL-L-PHENYLALANINE LOWER ALKYL ESTER

BACKGROUND OF THE INVENTION

1. Field of the Invention

This invention relates to a method for purifying an α-L-aspartyl-L-phenylalanine lower alkyl ester (hereinafter referred to as α-APE).

2. Description of the Prior Art

The α-APE, particularly α-L-aspartyl-L-phenylalaninemethyl ester (hereinafter referred to as α-APM), has a strong sucrose-like sweetness and thus has been drawing attention as novel sweetening.

Therefore, there have been proposed many methods for synthesizing the α-APE including, for example, a method of manufacturing it by directly bonding an L-phenylalaninemethyl ester and a strong acid addition salt of aspartic acid anhydride. Such a method, however, inevitably produces by-products such as a tripeptide ester which is formed by the coupling of the product α-APE with an additional molecule of aspartic acid, a tripeptide resulting from the tripeptide ester by the hydrolysis of an ester group, α-L-aspartyl-L-phenylalanine (hereinafter referred to as α-AP) resulting from the α-APE by the hydrolysis, a diketopiperazine derivative (hereinafter referred to as DKP), especially 3-benzyl-6-carboxymethyl-2,5-diketopiperazine, which results from the α-APE by the ring formation.

It is also known to obtain the α-APE by condensating an N-protected L-aspartic acid and an L-phenylalanine lower alkyl ester by an enzyme and then by removing the protection group. This method produces by-products to a lesser degree. However, even with this method employed, it is still hardly possible to substantially prevent α-AP and DKP production.

Conceivable methods for separating and purifying the α-APE would include a method of purifying the α-APE through a crystallization process. In this case, however, these by-products may tend to form mixed crystals because of their similarity with the α-APE in chemical structure. Therefore, these by-products still can be hardly removed by such a method.

In another known method for removing these by-products, an anion exchange resin of a specific type is employed. This method is disclosed in examined Japanese patent publication No. 35660/1977. In accordance with this method, these by-products are brought into contact with an anion exchange resin of an acetate or a formate type in an aqueous solvent to selectively remove them by adsorption. It is disclosed that it should not be possible to attain the object purification in the method if an other type of anion exchange resin than the organic acid addition type is employed because the impurity of the dipeptide ester material, i.e. an α-APE, would rather decrease if an anion exchange resin of such a type is used.

The present inventors conducted further studies on processes for purifying an α-APE using an anion exchange resin. As a result of the studies, they discovered that the purification of the α-APE using an anion exchange resin which had been believed to be impossible unless an anion exchange resin of an organic weak acid addition type was used could be quite effectively carried out by using a Cl-type anion exchange resin. This discovery has led to the present invention.

SUMMARY OF THE INVENTION

It is therefore a general object of the present invention to provide a method for purifying an α-APE which contains impurities wherein the α-APE is brought into contact with a Cl-type anion exchange resin to remove the impurities by the adsorption of the anion exchange resin.

In accordance with the method of the present invention, the purification can be most effectively carried out with a crude α-APE which is obtained by the above stated method using an enzyme.

Unlike the α-APE which is obtained by the above stated conventional chemical manufacturing method, the α-APE obtained by this method mainly contains α-AP and a DKP as main impurities and contains only a slight amount of other impurities derived from the starting materials. Therefore, it is particularly important for an α-APE obtained by such a method to effectively remove α-AP and the DKP.

When an α-APE containing α-AP and the DKP is allowed to contact with a Cl-type anion exchange resin in an aqueous solvent in accordance with the invented method, the α-APE is not adsorbed at all by the resin while the α-AP and the DKP are adsorbed by the resin.

The resin to be used in accordance with the present invention is an anion exchange resin in the Cl-type without any particular restriction. However, it is preferable to use a strongly basic anion exchange resin.

The aqueous solvent to be used in accordance with the present invention is water or a mixture of water and an inert organic solvent which is soluble in water such as methanol, ethanol, propanol, acetone, methyl ethyl ketone, tetrahydrofuran, dioxane, ethylene glycol, dimethylformamide, or the like.

The contact between the anion exchange resin and an α-APE solution containing impurities may be carried out by an ordinary method. For example, the solution is passed through a column that is filled with the resin or the solution and the resin are brought into contact with each other within a vessel by stirring or agitation.

The temperature at the time of the contact does not substantially effect on adsorption of impurities. However, highly elevated temperature presents a problem in respect to the stability of the α-APE. Therefore, the temperature is usually within a range from 0° to 70° C.

The recovery of a purified α-APE from the aqueous solution treated with the Cl-type anion exchange resin may be carried out by a conventional method, such as an ordinary crystallization method. When an α-APE solution of relatively low concentration is treated, the α-APE is recovered, for example, by condensing and then cooling the solution. When a relatively concentrated solution is treated at an elevated temperature, the α-APE can be recovered by merely cooling the solution.

In the case of the above stated method of using an anion exchange resin of the organic weak acid salt type, the low degree of dessociation of the organic weak acid necessitates the use of a great quantity of the organic weak acid or its salt of relatively high concentration when the adsorbed impurities are desorbed from the resin for the repeated use. To avoid such an inconvenience, it should be necessary to convert the anion exchange resin into an OH-type at first and then into an organic weak acid salt type.

Whereas, the Cl-type anion exchange resin employed in accordance with the invented method can be readily regenerated by means of a solution containing chloride ions such as hydrochloric acid or brine.

Further, with the former method employed, organic acid ions which have a greater affinity for the α-APE are introduced to enter the treated α-APE solution by ion exchange. Whereas, in the case of the invented method, only chloride ions enter the treated solution which ions are readily removable during a process such as crystallization process or the like, and therefor, the α-APE can be readily recovered thereafter.

It is another advantage of the invented method that the disposal of a waste liquid can be more easily carried out, because the system arranged in accordance with the invented method does not have the organic acid or its salt.

All will be understood from the foregoing description, the invented method readily permits selective removal of impurities, particularly the DKP and α-AP, contained in the α-APE through a simple operation.

The above and further object, features and advantages of the invention will become apparent from the following detailed description of embodiment examples.

DETAILED DESCRIPTION OF PREFERRED EMBODIMENTS

In the embodiment examples given below, analysis was made by high speed liquid chromatography, with measurement conducted under the following conditions:

Apparatus Used

For α-APM: "TSK GEL LS-170" (trademark), 5μ, packed in a column of inner dia. 7.5 mm×20 cm length For α-AP and DKP: "TSK GEL IEX-210" (trademark), 5μ, packed in a column of inner dia. 4.0 mm×10 cm length and "TSK GEL LS-170" (trademark), 5μ, packed in a column of inner diameter 7.5 mm×40 cm length.

Eluent: An aqueous solution of sodium acetate
Rate of flow: 0.9 ml/min
Measuring temperature: 25° C.
Detector: A UV Detector "UVIDEC-III" (manufactured by Nippon Bunko K.K.)
Measuring wave length: 256 nm

EXAMPLE 1

A treating solution was prepared by dissolving 200 mg of α-APM and 20 mg of a DKP (3-benzyl-6-carboxymethyl-2,5-diketopiperazine) in 50 ml of water. This solution was equivalent to a solution prepared by dissolving 220 mg of a crude α-APM containing 9.1% of the DKP. To this solution was added 2.0 g (dry) of a Cl-type strongly basic anion exchange resin (trademark: Amberlite IRA-410) and was stirred at 30° C. for 20 min by using a magnetic stirrer. The reaction solution was then filtrated and the resin was washed with 20 ml of water. Then, the mixture of the filtrate and the washing water was subjected to above stated high speed chromatography analysis to determine the quantities of α-APM and the DKP contained. It was found that the mixture contained 187 mg of α-APM and 0.70 mg of the DKP. The ratio of the DKP content to the sum total quantity of α-APM and the DKP was 0.37%. The recovery of α-APM was 93.5%.

EXAMPLE 2

A treating solution was prepared by dissolving 400 mg of α-APM, 20 mg of a DKP (3-beuzyl-6-carboxymethyl-2,5-diketopiperazine) and 20 mg of α-AP in 100 ml of water. This solution was equivalent to a solution obtained by dissolving a crude α-APM containing 4.5% of the DKP and 4.5% of α-AP. To this solution was added 4.0 g (dry) of a Cl-type strongly basic anion exchange resin (trademark: Amberlite IRA-900). Agitation was carried out an incubator at 30° C. for 20 min. The reaction solution was filtrated and the resin was washed with 50 ml of water. Then, the mixture of filtrate and the washing water was subjected to the analytical process as mentioned in the foregoing for the determination to find that the mixture contained 398 mg of α-APM, 1.1 mg of the DKP and 1.4 mg of α-AP. The contents of the DKP and α-AP relative to the sum total quantity of the α-APM, DKP and α-AP were 0.27% and 0.35%, respectively. The recovery of α-APM was 99.5%.

EXAMPLE 3

A treating solution of the same composition as that of Example 2 was prepared. To this was added 4.0 g (dry) of a Cl-type anion exchange resin (trademark: Amberlite IRA-410). Then, subsequent processes were carried out in the same manner as in Example 2. The results of analysis indicated that the mixture of the filtrate and the washing water contained 383 mg of α-APM and 1.0 mg of the DKP while there was found no appreciable α-AP. The DKP content based on the sum total quantity of α-APM and the DKP was 0.26%. The recovery of α-APM was 95.8%.

EXAMPLE 4

A treating solution was prepared by dissolving 400 mg of α-APM, 40 mg of a DKP (3-benzyl-6-carboxymethyl-2,5-diketopiperazine) and 40 mg of α-AP in 100 ml of water. This solution was equivalent to a solution of a crude α-APM containing 8.33% each of the DKP and α-AP. To this solution was added 4.0 g (dry) of a Cl-type strongly basic anion exchange resin (trademark: Amberlite IRA-410) and subsequent process were carried out in the same manner as in Example 2. The results of analysis indicated that the mixture of the filtrate and the washing water contained 400 mg of α-APM, 1.8 mg of the DKP and 2.3 mg of α-AP. The contents of the DKP and α-AP based on the sum total quantity of α-APM, DKP and α-AP were 0.45% and 0.57%, respectively. α-APM was completely recovered.

EXAMPLE 5

A cylindrical column measuring 12 mm in inner dia. was filled with 10 g (dry) of a Cl-type strongly basic anion exchange resin (trademark: Amberlite IRA-410) which occupied a volume of 18.3 ml in the column. A treating solution was prepared by dissolving 5.0 g of α-APM, 100 mg of a DKP (3-benzyl-6-carboxymethyl-2,5-diketopiperazine) and 100 mg of α-AP in 400 ml of water. The solution was equivalent to a solution of a crude α-APM containing 1.9% each of the DKP and α-AP.

The treating solution was allowed to break through the resin column at SV=12 and at 29° C. Then, the resin was washed with 100 ml of water. A part of thus obtained break-through solution was aliquoted and subjected to the analytical process as mentioned in the foregoing for the determination. It was found that there was contained 5.0 g of α-APM (100% recovery) while neither DKP nor α-AP was detected. The thus obtained break-through solution was condensed under reduced pressure and 255 g of the solvent was removed by distillation. Following to this, the residual was allowed to crystallize by cooling it over-night in a refrigerator. By this, 2.49 g (49.8%) of α-APM crystals were obtained. Neither DKP nor α-AP was detected from the crystals.

EXAMPLE 6

A treating solution was prepared by dissolving 5.0 g of α-APM, 100 mg of a DKP (3-benzyl-6-carboxymethyl-2,5-diketopiperazine) and 100 mg of α-AP in a mixture of 350 ml of water and 50 ml of methanol. This solution was corresponding to a solution prepared by dissolving a crude α-APM containing each 1.9% of the DKP and α-AP. The treating solution was processed in the same manner as in Example 5 with 10 g of the same resin as used in Example 5.

Analysis of thus obtained break-through solution was conducted to find that 4.87 g of α-APM (97.5%) was contained therein while neither α-AP nor the DKP was detected in the solution.

The break-through solution was condensed by distillation under reduced pressure and, after removal of 237 g of the solvent, was cooled in a refrigerator over-night for the crystallization. By this, 2.90 g (57.9%) of α-APM was obtained. Neither α-AP nor DKP was detected from the crystals.

EXAMPLE 7

A treating solution was prepared which had the same composition as in Example 2. To this solution was added 4.0 g (dry) of a moderately basic anion exchange resin (trademark: Amberlite IRA-68) which was converted into a hydrochloride type and the processes were carried out in the same manner as in Example 2.

The results of analysis indicated that the resulting mixture of filtrate and washing water contained 393 mg of α-APM, 14.4 mg of the DKP and 6.5 mg of α-AP. The ratios of the DKP and α-AP contents to the sum total quantity of α-APM, DKP and α-AP were 3.5% and 1.6% respectively. The recovery of α-APM was 97.5%.

EXAMPLE 8

A treating solution was prepared which had the same composition as in Example 2. To this solution was added 4.0 g (dry) of a weakly basic anion exchange resin (trademark: Amberlite IR-45) which was converted into hydrochloride type. Then, subsequent processes were carried out in the same manner as in Example 2.

The results of analysis indicated that the mixture of the filtrate and washing water contained 390 mg of α-APM, 6.3 mg of the DKP and 4.9 mg of α-AP. The ratios of DKP and α-AP contents to the sum total quantity of α-APM, DKP and α-AP were 1.6% and 1.2%, respectively. The recovery of α-APM was 97.5%.

EXAMPLE 9

A treating solution was prepared by dissolving 4.0 g of α-APM, 100 mg of L-aspartic acid and 100 mg of N-benzyloxycarbonyl-L-aspartic acid in 400 ml of water. This solution was equivalent to a solution obtained by dissolving a crude α-APM containing each 2.4 of L-aspartic acid and N-benzyloxycarbonyl-L-aspartic acid. The treating solution was processed with 14 g of the same resin as used in Example 5 and in the same manner as in Example 5.

The results of analysis of thus obtained break-through solution indicated that it contained 3.96 g (99%) of α-APM and neither L-aspartic acid nor N-benzyloxycarbonyl-L-aspartic acid was detected.

EXAMPLE 10

N-Benzyloxycarbonyl-α-L-aspartyl-L-phenylalaninemethyl ester was obtained by carrying out a condensation of N-benzyloxycarbonyl-L-aspartic acid and L-phenylalaninemethyl ester using thermoase, a proteolytic enzyme. Following to this, 316 g of an aqueous solution of α-APM was obtained by carrying out a hydrogenolysis reaction to remove a benzyloxycarbonyl group. This solution contained 25.10 g of α-APM, 0.533 g of a DKP (3-benzyl-6-carboxymethyl-2, 5-diketopiperazine), 0.249 g of α-AP and 0.055 g of L-aspartic acid and was equivalent to an aqueous solution of a crude α-APM containing the DKP, α-AP and L-aspartic acid in quantities of 2.0, 0.94 and 0.21%, respectively.

A cylindrical glass tube measuring 2 cm in inner dia. was filled with 15.5 g (dry) of a strongly basic anion exchange resin (Amberlite IRA-410 trademark) in Cl-type. Water was added to the above stated treating solution to make the total quantity 674 g. While the solution was kept at 55° C., the solution was allowed to brake through the resin column at SV=5.2. After the break-through process, the resin column was washed with 65 ml of water. Then, 719 g of the effluent consisting of the break-through solution and the washing water was left standing in a refrigerator over-night for the crystallization. The crystals were collected by filtration and were washed with 36 ml of water to obtain 19.6 g (78.0%) of crystalline α-APM. The crystals contained 25 mg and 8 mg of the DKP and α-AP, respectively. The remaining mixture of filtrate and washing water contained 5.24 g of α-APM while 28 mg of the DKP and 7 mg of α-AP were respectively contained in the solution. Further, L-aspartic acid was detected neither in the crystals nor in the filtrate mixture.

The ratios of the DKP and α-AP contents to the total quantity of α-APM, DKP and α-AP contained in the effluent from the column were 0.2% and 0.1% respectively. The recovery of α-APM was 98.8%.

What is claimed is:

1. A method for purifying an α-L-aspartyl-L-phenylalanine lower alkyl ester containing impurities including α-L-aspartyl-L-phenylalanine and 3-benzyl-6-carboxymethyl-2,5-diketopiperazine, and which comprises contacting the α-L-aspartyl-L-phenylalanine lower alkyl ester with a Cl-type anion exchange resin in an aqueous solvent, thereby adsorbing the impurities in the anion exchange resin and recovering the α-L-aspartyl-L-phenylalanine lower alkyl ester in a purified state.

2. A method according to claim 1, wherein the lower alkyl group of said α-L-aspartyl-L-phenylalanine lower alkyl ester is a methyl group.

3. A method according to claim 1 or 2 wherein said aqueous solvent is an aqueous solution.

4. A method according to claim 3, wherein said aqueous solvent is an aqueous solution of methanol.

* * * * *